United States Patent
Berube

(10) Patent No.: US 6,823,218 B2
(45) Date of Patent: *Nov. 23, 2004

(54) MONOPOLE TIP FOR ABLATION CATHETER AND METHODS FOR USING SAME

(75) Inventor: Dany Berube, Milpitas, CA (US)

(73) Assignee: AFX, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/904,156

(22) Filed: Jul. 31, 2001

(65) Prior Publication Data

US 2002/0111613 A1 Aug. 15, 2002

Related U.S. Application Data

(63) Continuation of application No. 09/321,666, filed on May 28, 1999, now Pat. No. 6,277,113.

(51) Int. Cl.[7] ................................................ A61N 1/00
(52) U.S. Cl. ........................ 607/156; 606/33; 607/101
(58) Field of Search ............................... 607/101, 102, 607/122, 154–156; 606/33, 34, 41

(56) References Cited

U.S. PATENT DOCUMENTS

| | | | |
|---|---|---|---|
| 4,641,649 A | * 2/1987 | Walinsky et al. | ............. 606/33 |
| 4,643,186 A | 2/1987 | Rosen et al. | |
| 5,230,349 A | 7/1993 | Langberg | |
| 5,246,438 A | 9/1993 | Langberg | |
| 5,301,687 A | 4/1994 | Wong et al. | |
| 5,314,466 A | 5/1994 | Stern et al. | |
| 5,358,515 A | 10/1994 | Hurter et al. | |
| 5,370,644 A | 12/1994 | Langberg | |
| 5,405,346 A | 4/1995 | Grundy et al. | |
| 5,683,382 A | * 11/1997 | Lenihan et al. | ............... 606/33 |
| 5,810,803 A | * 9/1998 | Moss et al. | ................. 606/33 |
| 5,904,709 A | 5/1999 | Arndt et al. | |
| 6,051,018 A | * 4/2000 | Larsen | ....................... 607/154 |
| 6,097,985 A | 8/2000 | Kasevich et al. | |
| 6,226,553 B1 | * 5/2001 | Carl et al. | ................... 607/101 |
| 6,277,113 B1 | 8/2001 | Berube | |

* cited by examiner

*Primary Examiner*—Michael Peffley
(74) *Attorney, Agent, or Firm*—Fenwick & West LLP

(57) ABSTRACT

An ablation catheter apparatus with a monopole antenna that is arranged to provide a relatively uniform electric field and a method for using such an ablation catheter apparatus are disclosed. According to one aspect of the present invention, an ablation catheter includes an elongated flexible tubular member that is adapted to be inserted into the body of a patient, and a transmission line that is disposed within the tubular member. The transmission line has a distal end and a proximal end which is arranged to be connected to an electromagnetic energy source. The catheter also includes a monopole antenna with tip section and a body section that includes a distal end and a proximal end. The tip section and the body section are arranged to produce a relatively uniform electric field around the monopole antenna which is sufficiently strong to cause tissue ablation. The proximal end of the body section of the monopole antenna is arranged to be electrically coupled to the transmission line.

8 Claims, 6 Drawing Sheets

US 6,823,218 B2

MONOPOLE TIP FOR ABLATION CATHETER AND METHODS FOR USING SAME

This application is a Continuation of U.S. patent application Ser. No. 09/321,666, filed May 28, 1999, now U.S. Pat. No. 6,277,113 which is incorporated herein by reference, in its entirety.

BACKGROUND OF THE INVENTION

1. Field of Invention

The present invention relates generally to ablation catheter systems that use electromagnetic energy in the microwave frequency range to ablate internal bodily tissues. More particularly, the present invention relates to a monopole tip for a catheter that enables distal fire capabilities while enabling a relatively even electromagnetic field to be created at the sides of the monopole tip to facilitate the ablation of cardiac tissue.

2. Description of the Related Art

Catheter ablation is a therapy that is becoming more widely used for the treatment of medical problems such as cardiac arrhythmias, cardiac disrhythmias, and tachycardia. Most presently approved ablation catheter systems utilize radio frequency (RF) energy as the ablating energy source. However, RF energy has several limitations which include the rapid dissipation of energy in surface tissues. This rapid dissipation of energy often results in shallow "burns," as well as a failure to access deeper arrhythmic tissues. As such, catheters which utilize electromagnetic energy in the microwave frequency range as the ablation energy source are currently being developed. Microwave frequency energy has long been recognized as an effective energy source for heating biological tissues and has seen use in such hyperthermia applications as cancer treatment and the preheating of blood prior to infusions. Catheters which utilize microwave energy have been observed to be capable of generating substantially larger lesions than those generated by RF catheters, which greatly simplifies the actual ablation procedures. Some catheter systems which utilize microwave energy are described in the U.S. Pat. No. 4,641,649 to Walinsky; U.S. Pat. No. 5,246,438 to Langberg; U.S. Pat. No. 5,405,346 to Grundy, et al.; and U.S. Pat. No. 5,314,466 to Stern, et al., each of which is incorporated herein by reference in its entirety.

Cardiac arrhythmias, which may be treated using catheter ablation, are generally circuits, known as "reentry circuits," which form within the chambers of the heart. As is known to those skilled in the art, reentry circuits are abnormal electrical pathways that may form in various areas of the heart. For example, reentry circuits may form around veins and/or arteries which lead away from and to the heart. Cardiac arrhythmias may occur in any area of the heart where reentry circuits are formed.

The catheters used for treatment of cardiac arrhythmias, disrhythmias, and tachycardia may have a variety of different antenna configurations to create electromagnetic fields used in ablation. Some catheters have antennas that essentially protrude from the distal ends of the catheters. In other words, some catheters have antennas which form the distal tips of the catheters. A monopole antenna is typically configured to form the distal tip of a catheter.

FIG. 1a is a diagrammatic representation of a distal end of a catheter with a monopole antenna at its tip. A distal end 102 of a catheter has a monopole antenna 108 at its tip. As shown, monopole antenna 108 has a rounded shape, and is coupled to a center conductor 112 of a co-axial transmission line 116. Typically, monopole antenna 108 is formed from a metallic material. Distal end 102 of the catheter may also include electrodes 120, which may be used for mapping processes, that may be coupled to processing equipment (not shown) using ECG wires 122.

Monopole antenna 108 is often arranged to be used in ablating tissue. Center conductor 112 transmits energy, e.g., electromagnetic energy, to monopole antenna 108 to allow an electromagnetic field to be formed with respect to monopole antenna. FIG. 1b is a diagrammatic representation of a monopole antenna, i.e., monopole antenna 108 of FIG. 1a, shown with electromagnetic field lines. Electromagnetic field lines 130 generally radiate from monopole antenna 108 in a substantially ellipsoidal pattern. Hence, near sides 134, "hot spots" 138 of electromagnetic energy are typically formed. Hot spots 138 are generally associated with the highest amounts of electromagnetic energy radiated by monopole antenna 108. The existence of hot spots 138 causes certain portions of a myocardium of heart, for example, such as those that are substantially contacted by a hot spot to be ablated more than other portions.

When an ablation procedure is performed using monopole antenna 108, the depth of cuts formed may not be uniform, since electromagnetic field lines 130 are not uniform. That is, the shape, or profile, of electromagnetic field lines 130 are such that when ablation is performed, the depth associated with the ablation may not be even. The lack of even depth in an ablation procedure may cause the ablation, e.g., an ablation in the myocardium of a heart, to be unsuccessful, as all of the cardiac tissue may not be effectively ablated. Hence, the ablation procedure may have to be repeated, which is both time-consuming and inefficient.

Therefore, what is needed is a monopole antenna structure for use with an ablation catheter that efficiently allows tissue to be ablated. More specifically, what is desired is a monopole antenna structure that is capable of producing a relatively field, e.g., electromagnetic field, a deep lesion, and a microwave power deposition at the tip of a catheter, i.e., a tip-firing catheter.

SUMMARY OF THE INVENTION

The present invention relates generally to an ablation catheter with a monopole antenna that is arranged to provide an electric field that is able to produce a deep lesion, e.g., in the myocardium or a heart, and has a tip-firing capability. According to one aspect of the present invention, an ablation catheter includes an elongated flexible tubular member that is adapted to be inserted into the body of a patient, and a transmission line that is disposed within the tubular member. The transmission line has a distal end and a proximal end which is arranged to be connected to an electromagnetic energy source. The catheter also includes a monopole antenna with tip section and a body section that includes a distal end and a proximal end. The tip section and the body section are arranged to produce a relatively uniform electric field around the monopole antenna which is sufficiently strong to cause deep tissue ablation. The proximal end of the body section of the monopole antenna is arranged to be electrically coupled to the transmission line.

In one embodiment, the transmission line is a coaxial cable, which has a center conductor and an outer conductor. In such an embodiment, the proximal end of the monopole antenna is arranged to be electrically coupled to the center conductor. In another embodiment, the body section of the monopole antenna is tapered such that the diameter at the proximal end of the body section of the monopole antenna is smaller than the diameter at the distal end of the body section of the monopole antenna.

According to another aspect of the present invention, an antenna structure arranged to be used in an ablation catheter has a longitudinal axis, and includes a body section with a first end and a second end, a tip section, and a transition section. The body section is sized such that the axial cross-sectional area about the longitudinal axis of the second end is smaller than the axial cross-sectional area about the longitudinal axis of the first end. The second end is arranged to be electrically coupled to a transmission line, and the body section is shaped to allow a relatively uniform electric field to be formed with respect to the antenna structure.

The tip section has a proximal portion that has an axial cross-sectional area about the longitudinal axis which is greater than or approximately equal to the axial cross-sectional area of the first end, and the transition section is disposed between the proximal portion and the first end.

In one embodiment, the first end has a diameter that is greater than the diameter of the second end, and the proximal portion has a diameter that is greater than or equal to the diameter of the first end. In such an embodiment, the tip section may have a diameter that is less than the diameter of the first end.

In accordance with still another aspect of the present invention, a microwave ablation catheter includes an elongated flexible tubular member, which has a distal portion, a proximal portion, and a longitudinal catheter axis, and is adapted to be inserted into a vessel in the body of a patient. The microwave ablation catheter also includes a transmission line with a proximal end and a distal end. The transmission line is disposed within the tubular member, and the proximal end of the transmission line is suitable for connection to an electromagnetic energy source. A monopole antenna which is part of the microwave ablation catheter is coupled to the transmission line for generating an electric field sufficiently strong to cause tissue ablation, and includes a frusto-conically shaped emitting surface with an axis that is substantially parallel to the longitudinal catheter axis. In one embodiment, the monopole antenna further includes a rounded distal emitter surface. In such an embodiment, the antenna may also include a trough region between the frusto-conically shaped emitting surface and the distal emitter surface, as well as an encapsulating material that encapsulates the trough and frusto-conically shaped emitting surface such that the trough forms an anchor for the encapsulating material.

These and other advantages of the present invention will become apparent upon reading the following detailed descriptions and studying the various figures of the drawings.

DETAILED DESCRIPTION OF THE DRAWINGS

The invention may best be understood by reference to the following description taken in conjunction with the accompanying drawings in which.

BRIEF DESCRIPTION OF THE EMBODIMENTS

When the electromagnetic field associated with an antenna in an ablation catheter is not uniform, the depth of an ablation formed in cardiac tissue using the catheter is often uneven. Ablation catheters with conventional monopole antennas generally do not emit uniform electric fields. Instead, the contour of electric field lines, as well as hot spots in the electric field around a monopole antenna, are such that ablation of cardiac tissue, as for example in a myocardium of a heart, are often uneven. As a result, the ablation of the tissue may not be successful.

An ablation catheter that has a monopole antenna which is shaped to enable a substantially uniform field, e.g., electromagnetic or electric field, to be formed around the monopole antenna allows the depth of an ablation of tissue to occur substantially uniformly In addition, such a monopole antenna allows the catheter to have forward firing, or tip-firing, capabilities. That is, the distal tip of the monopole antenna may also be used to ablate tissue.

When the depth of an ablation is relatively uniform, i.e., has a substantially uniform depth, an overall ablation process may be more efficiently performed, as it may be unnecessary to repeatedly ablate the same area of tissue to obtain an even depth of ablation. When an overall ablation process is more efficient, in that the time spent performing ablation may be reduced.

Figure 1A:
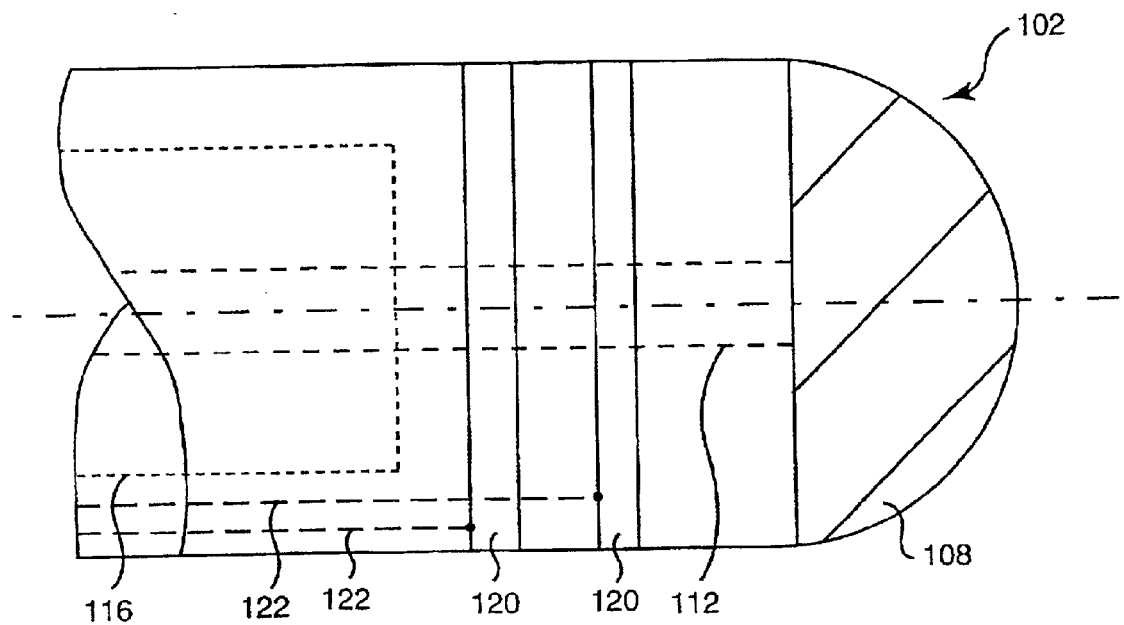
FIG. 1a is a diagrammatic representation of a distal end of a catheter with a monopole tip.
Figure 1B:
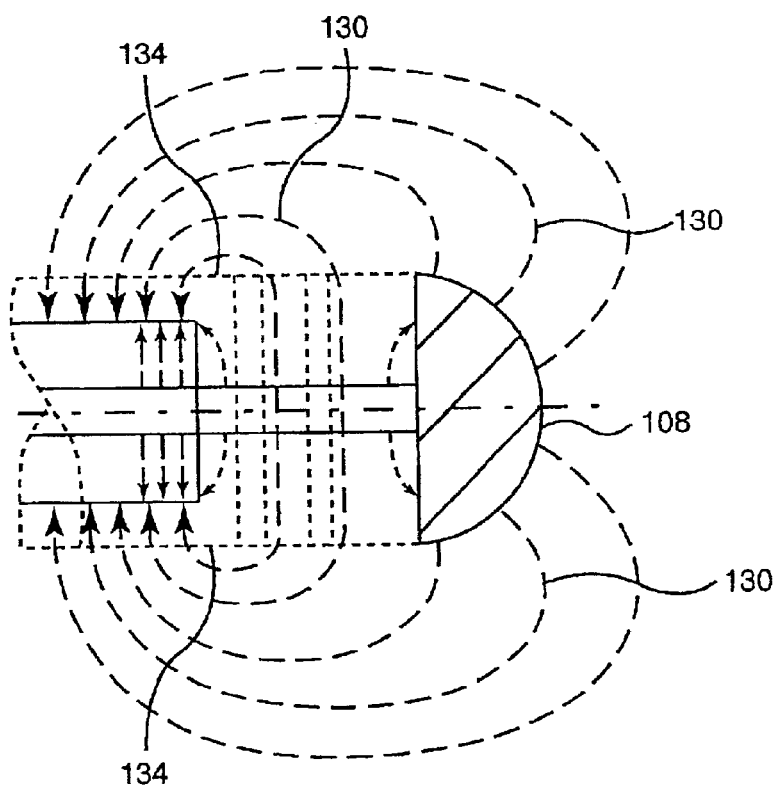
FIG. 1b is a diagrammatic representation of a monopole antenna, i.e., monopole antenna 108 of FIG. 1a, shown with electromagnetic field lines.
Figure 2A:
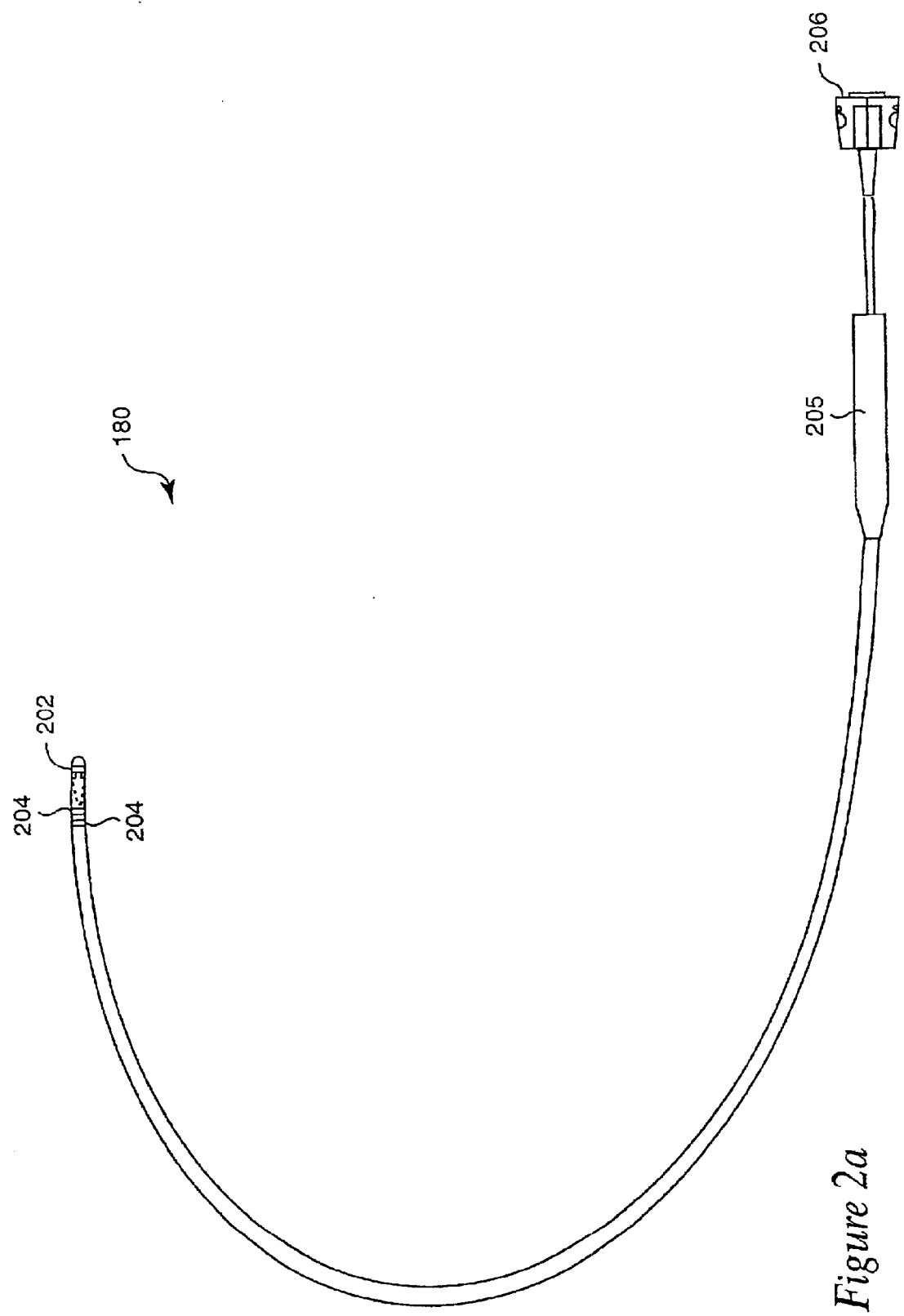
FIG. 2a is a diagrammatic representation of an ablation catheter in accordance with an embodiment of the present invention.

A monopole antenna which includes a tip section and a tapered body section enables hot spots in the electromagnetic field formed around the body section to be substantially eliminated. FIG. 2a is a diagrammatic representation of an ablation catheter with a monopole antenna, which includes a tip section and a tapered body section, in accordance with an embodiment of the present invention. An ablation catheter 180, which is suitable for use as a microwave ablation catheter, is generally arranged to be introduced into the body of a patient through a blood vessel, e.g., the femoral vein. Catheter 180 may be considered to be an overall elongated, flexible, tube. It should be appreciated that for ease of illustration, catheter 180 has not been drawn to scale.

Since catheter 180 is arranged to be used within the body of a patient, materials used to form catheter 180 are typically biocompatible materials. Suitable biocompatible materials used to form catheter 180 include, but are not limited to medical grade polyolefins, fluoropolymers, polyurethane, polyethylene, or polyvinylidene fluoride. In one embodiment, a PEBAX resin, which is available commercially from Elf Atochem of Germany, may be used in the formation of catheter 180.

Catheter 180 includes a monopole antenna 202 from which an electric field may be emitted to cause ablation. As shown, monopole antenna 202 is located at the distal end of catheter 180. Monopole antenna 202, which may be machined from a material such as stainless steel using a mill or a lathe, will be discussed below with reference to FIG. 2b. Typically, once catheter 180 is introduced into the body of a patient, catheter 180 is manipulated through a blood vessel and into the heart such that monopole antenna 202 may be positioned within a cardiac chamber in which an ablation procedure is to be performed.

Catheter 180 also includes electrodes 204 which are positioned on catheter 180 such that they are located proximally with respect to monopole antenna 202. Electrodes 204 are generally arranged to detect electro-physiological signals from cardiac tissue. Hence, electrodes 204, which are generally electrode bands, may be used to map the relevant region of the heart, i.e., the portion of the heart with which an ablation procedure is associated, prior to or after an ablation procedure. Electrodes 204 may also be used to aid in positioning catheter 180 during an ablation procedure. In general, although electrodes 204 may be formed from any suitable material which has biocompatible characteristics, electrodes 204 are typically formed from materials which include, but are not limited to, stainless steel and iridium platinum.

A handle 205 is often located near a proximal end of catheter 180, although it should be appreciated that handle 205 is not necessarily included as a part of catheter 180. Handle 205 is arranged to enable a user, i.e., an individual who is performing an ablation procedure on a patient, to grip and to manipulate catheter 180. In the described embodiment, a connector 206 is located on catheter 180 such that connector 206 is proximal to handle 205. Connector 206 is arranged to couple a transmission line (not shown), which is located within catheter 180, to a power supply, or similar device, that is designed to generate controlled electromagnetic energy.

Figure 2B:
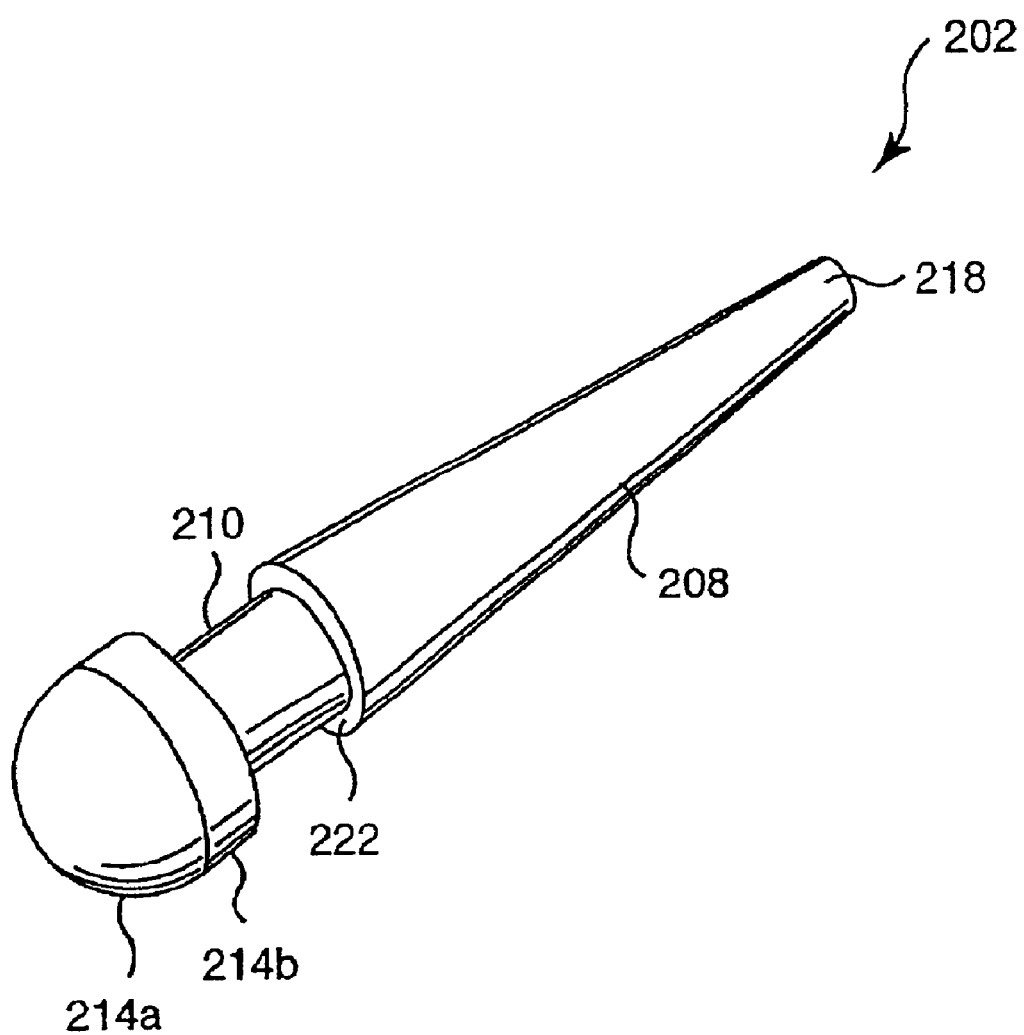
FIG. 2b is a perspective representation of a monopole antenna with a tapered configuration, i.e., monopole antenna 202 of FIG. 2a, in accordance with an embodiment of the present invention.

As mentioned above, monopole antenna 202 is arranged to provide an electric field, e.g., an electromagnetic field, to allow tissue to be ablated. In the described embodiment, monopole antenna 202 is shaped such that the electric field which is generated is effectively confined to the monopole region associated with monopole antenna 202. With reference to FIG. 2b, a monopole antenna with a tapered body section will be described in accordance with an embodiment of the present invention. FIG. 2b is a perspective representation of monopole antenna 202 of FIG. 2a. Monopole antenna 202 includes a body section 208, an intermediate section 210, and a tip section 214. In the described embodiment, body section 208 has a tapered shape, e.g., body section 208 is shaped substantially as a conical structure with no single apex point. That is, body section 208, which includes an emitting surface, may have a frusto-conical shape. A proximal end 218 of body section 208 generally has the smallest axial cross-sectional area, about a longitudinal axis of monopole antenna 202, associated with body section 208. By way of example, the diameter of proximal end 218, about the longitudinal axis of monopole antenna 202, is typically smaller than any other diameter, along the same axis, that is associated with body section 208.

Intermediate section 210 effectively separates body section 208 from tip section 214. One purpose of intermediate, or "trough," section 210 is to allow a material which is used to encase body section 208 to be anchored with respect to monopole antenna 202. In other words, intermediate section 210 is shaped such that a material which effectively encapsulates body section 208 and, further, at least part of intermediate section 210, is generally prevented from "peeling away" from intermediate section 210 and body section 208. The encapsulating material serves as a plug that holds monopole antenna 202 against a catheter, e.g., catheter 180 of FIG. 2a. In general, any suitable material may be used to form a plug that essentially encases body section 208. Such materials include, but are not limited to, Teflon, such as PolyTetraFluoroEthylene (PTFE), and Polyethylene (PE).

As shown, intermediate section 210 has an axial cross-sectional area that is less than the largest axial cross-sectional area associated with body section 208, i.e., the axial cross-sectional area associated with a distal end 222 of body section 208. In one embodiment, since intermediate section 210 and body section 208 have substantially circular cross-sectional areas, the diameter of intermediate section 210 is less than the diameter of distal end 222 of body section 208.

Tip section 214 typically includes a distal portion 214a and a proximal portion 214b. Distal portion 214a generally has a rounded shape. In the described embodiment, distal portion 214a has an approximately hemispherical shape. Proximal portion 214b has a substantially cylindrical shape, although it should be appreciated that the shape of proximal portion 214b may vary widely. In some embodiments, tip section 214 may include only distal portion 214a.

Generally, the dimensions associated with monopole antenna 202 may vary, depending upon the overall configuration of a catheter in which monopole antenna 202 is used. By way of example, the dimensions may vary in order to achieve electric field lines of a particular shape. Typically, body section 208 has a longitudinal length in the range of approximately 0.25 inches to approximately 0.4 inches, e.g., approximately 0.3 inches. The longitudinal length of intermediate section 210 may range from approximately 0.07 inches to approximately 0.10 inches, e.g., the longitudinal length of intermediate section 210 may be approximately 0.09 inches. Finally, the longitudinal length of tip section 214 may range from total length of approximately 0.08 inches to approximately 0.1 inches. In one embodiment, distal portion 214a of tip section 214 may have a longitudinal length of approximately 0.06 inches.

In addition to having a longitudinal length that may vary, monopole antenna 202 has diameters that may also be widely varied. As discussed above, body section 208 may have a tapered shape, e.g., a frusto-conical shape. Accordingly, the diameters along the longitudinal axis of body section 208 will generally vary. For example, the proximal end 218 of body section 208 may have a diameter which ranges between approximately 0.025 inches to approximately 0.04 inches, while the distal end 222 of body section 208 may have a diameter which ranges from approximately 0.06 inches to approximately 0.08 inches. It should be appreciated that the ranges of diameters may vary widely depending upon the requirements of an overall catheter system.

The diameter of intermediate section 210 may also be widely varied. In general, the diameter of intermediate section 210 may be any suitable diameter that is less than or equal to the diameter of distal end 222 of body section 208. However, the diameter of intermediate section 210 is preferably less than the diameter of distal end 222 of body section 208, in order for a plug to be securely formed around body section 208, as previously mentioned. By way of example, when distal end 222 of body section 208 has a diameter which ranges between approximately 0.6 inches and approximately 0.8 inches, then intermediate section 210 may have a diameter which ranges between approximately 0.04 inches to approximately 0.06 inches.

Like the other diameters associated with monopole antenna 202, the diameter associated with tip section 214 may also vary. In the described embodiment, the diameter associated with proximal portion 214b is substantially the same as a diameter associated with distal portion 214a. That is, when proximal portion 214b is approximately cylindrical in shape, and distal portion 214a is substantially hemispherical in shape, the diameters of proximal portion 214b and distal portion 214a may be approximately the same. For instance, the diameters may be in the range of approximately 0.08 inches to approximately 0.1 inches, although it should be understood that the diameters may be widely varied.

A monopole antenna such as monopole antenna 202 may be formed from substantially any conductive material. In general, monopole antennas are preferably formed from materials with relatively high conductivity characteristics. Since catheters which include monopole antennas are typically arranged to be inserted into human bodies, the monopole antennas are further formed from biocompatible materials, or are coated with a conductive biocompatible material, e.g., silver or platinum.

Figure 3A:
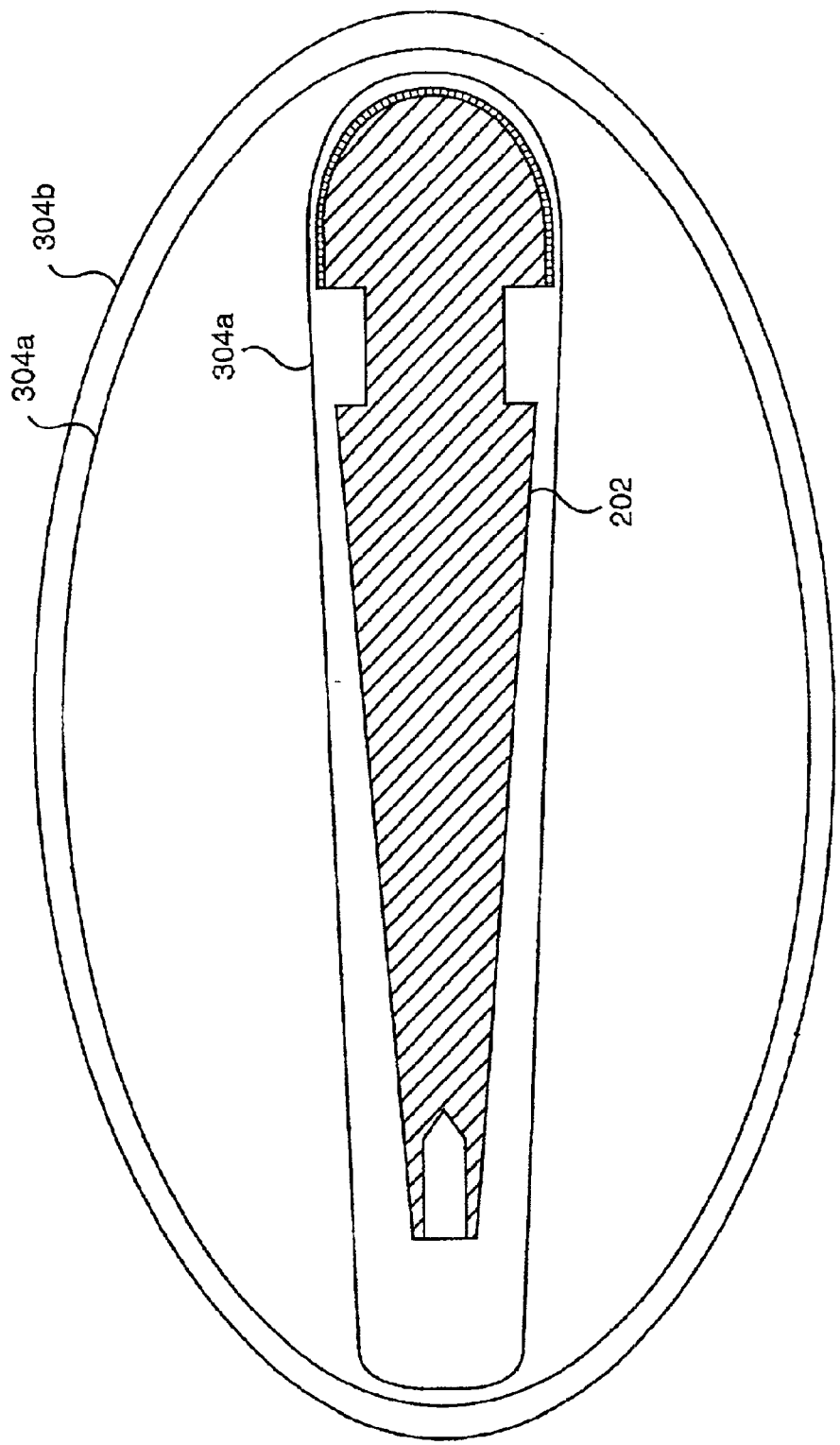
FIG. 3a is a diagrammatic side view representation of a monopole antenna, shown with a contour plot of the magnitude of electric field lines, in accordance with an embodiment of the present invention.

Monopole antenna 202, as mentioned above, is shaped to enable a substantially elliptical electromagnetic field to be formed around antenna 202. FIG. 3a is a diagrammatic side view representation of a monopole antenna, shown with contour lines associated with the magnitude of an associated electric field, in accordance with an embodiment of the present invention. Contour lines 304 are shown with respect to field propagation at ninety degrees of a cycle. As will be appreciated by those skilled in the art, a cycle is a phase shift of 360 degrees. The number of cycles per second will generally vary depending upon the frequency that is being used, which often varies depending upon the needs of a particular system. By way of example, in one embodiment, at a frequency of approximately 2.45 GigaHertz (GHz), the number of cycles per second is approximately $2.45 \times 10^9$.

For purposes of illustration, representative contour lines 304 of the magnitude of an electric field have been shown, although it should be appreciated that many more contour lines 304 associated with the magnitude of an electric field will generally exist. The magnitude of an electric field generally varies with the distance from monopole antenna 202. Specifically, the magnitude of an electric field decreases as the distance from monopole antenna 202 increases. For example, the magnitude of the portion of the electric field represented by contour line 304a is greater than the magnitude of the portion of the electric field represented by contour line 304c. In the described embodiment, the output power associated with monopole antenna 202 is approximately one Watt (W), and the magnitude of the electric field represented by contour line 304a is approximately 1000 Volts per meter (V/m). In such an embodiment, the magnitude of electric field line 304c may be approximately 500 V/m.

Ablation procedures that are performed with monopole antenna 202 may be more efficient than those performed using a conventional monopole antenna, in that the ablation of tissue is generally more even, e.g., the depth of an ablation made in cardiac tissue may be uniform. Specifically, the tip-firing capabilities of monopole antenna 202, as well as the deep penetration of the energy which emanates from monopole antenna 202, may allow for a more efficient treatment of flutters and tachycardias, for example.

Figure 3B:
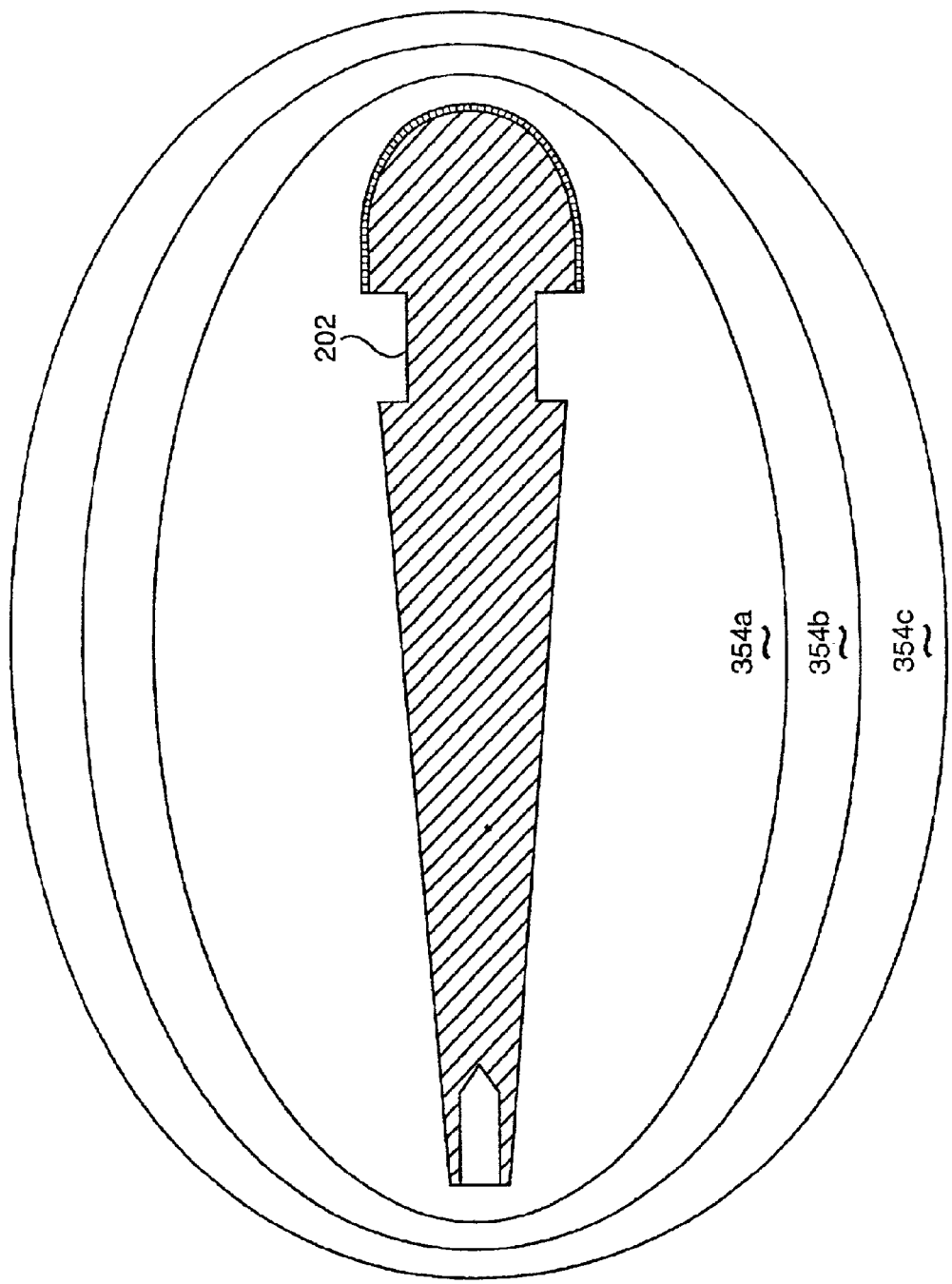
FIG. 3b is a diagrammatic side view representation of a monopole antenna, i.e., monopole antenna 302 of FIG. 3a, shown with relative specific absorption rates, in accordance with an embodiment of the present invention.

Monopole antenna 202 has an associated specific absorption rate (SAR), as will be understood by those skilled in the art. FIG. 3b is a diagrammatic side view representation of a monopole antenna, i.e., monopole antenna 302 of FIG. 3a, shown with a pattern specific absorption rates, in accordance with an embodiment of the present invention. The specific absorption rate associated with an antenna may be expressed as follows:

$$SAR = \frac{\sigma E^2}{2}$$

where $\sigma$ is the associated electrical conductivity at a particular frequency, e.g., approximately 2.45 GHz, and $E^2$ is the square of the magnitude of the electric field. As the magnitude of the electric field varies with distance from monopole antenna 202, the specific absorption rate also varies. Since the specific absorption rate is a function of the magnitude of the electric field, the specific absorption rate decreases as the distance from monopole antenna 202 increases.

In the described embodiment, specific absorption rate 354a is the highest rate associated with monopole antenna 202, while specific absorption rate 354c is the lowest rate associated with monopole antenna 202. The pattern of specific absorption rates have been shown as including three rates 354, it should be appreciated that more rates generally exist although, in some embodiments, fewer rates may be in existence.

Figure 4:
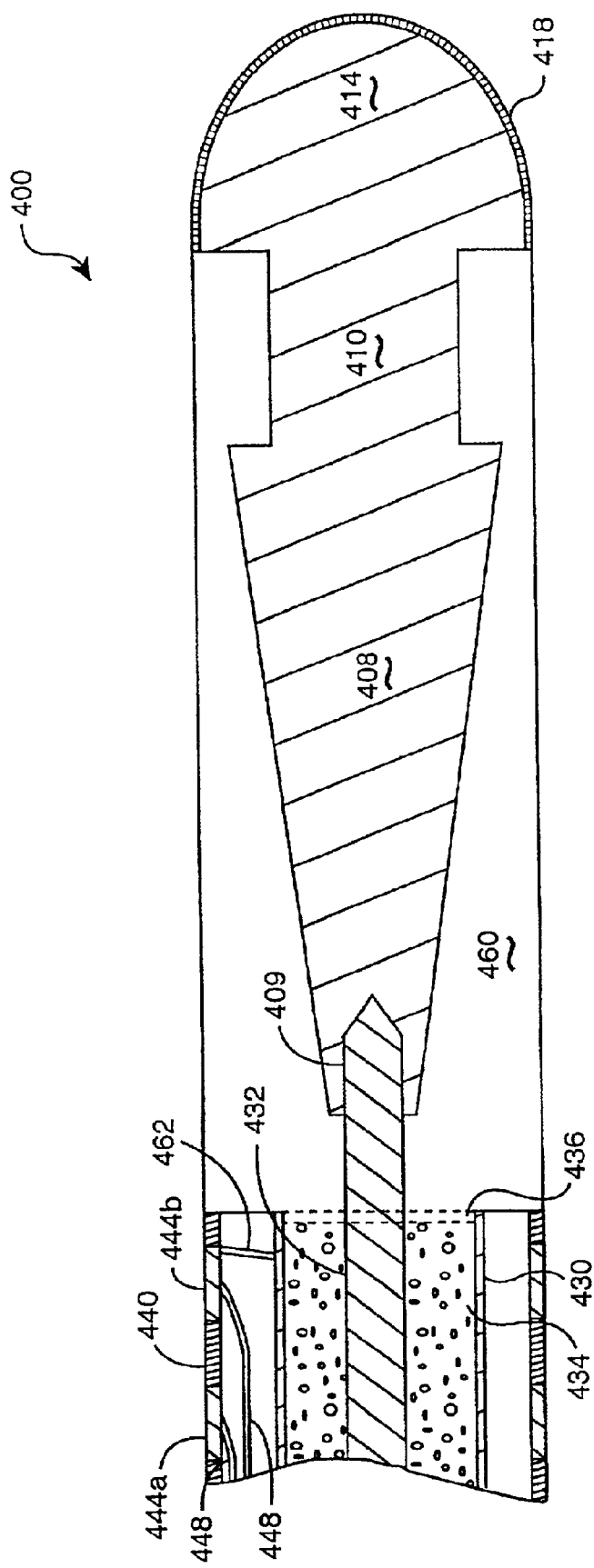
FIG. 4 is a diagrammatic cross-sectional representation of a distal end of a catheter which includes a monopole antenna in accordance with an embodiment of the present invention.

FIG. 4 is a diagrammatic cross-sectional representation of a distal end of a catheter which includes a monopole antenna in accordance with an embodiment of the present invention. A distal end 400 of a catheter includes a monopole antenna 402 which has a tapered body section 408, an intermediate section 410, and a tip section 414. For illustrative purposes, distal end 400 of catheter has not been drawn to scale. In the embodiment as shown, monopole antenna 402 also includes a surface finish 418, or coating, that covers the exterior of tip section 414. Surface finish 418 may be formed from a variety of different materials.

By way of example, surface finish 418 may be a silver plating. It should be appreciated that in another embodiment, monopole antenna 402 may not include a surface finish.

In the described embodiment, monopole antenna 402 is coupled to an electromagnetic wave generator that is external to the catheter (not shown) through a coaxial cable 430. Specifically, a center conductor 432 is electrically coupled to a proximal end of body section 408. As shown, body section 408 is bored out, e.g., includes a proximal bore 409, that is arranged to allow center conductor 432 to be electrically coupled to monopole antenna 402. In order to facilitate coupling of center conductor 432 to body section 408, center conductor 432 extends past an outer conductor 436, or a shield, of coaxial cable 430. A variety of different methods may be used to couple center conductor 432 to body section 408. By way of example, center conductor 432 may be coupled to body section 408 using a crimping process. An inner dielectric 434 of coaxial cable 430 serves to separate center conductor 432, which is arranged to carry electrical current, from shield 436 of coaxial cable 430. As will be appreciated by those skilled in the art, outer conductor 436 is often used for grounding purposes. Although coaxial cable 430 is arranged to provide power to monopole antenna 402, it should be appreciated that substantially any transmission line may be used in lieu of coaxial cable 430.

A flexible tubing 440, is effectively an outer sleeve that is formed over coaxial cable 430.

Typically, flexible tubing 440 may be made from any flexible, biocompatible material including, but not limited to, Teflon, polyethylene, and polyurethane. The thickness of flexible tubing 440 may vary widely depending upon the requirements of a particular catheter. By way of example, the thickness of flexible tubing 440 may vary between approximately 0.005 inches and approximately 0.015 inches.

Electrode bands 444 are often "pressed into" flexible tubing 440 such that electrode bands 444 may make contact with fluids and tissue that are external to the catheter. In general, electrode bands are electrically coupled to an external power supply (not shown) through electrode wires 448 which are located between flexible tubing 440 and co-axial cable 430. Electrode bands 444 may be used to monitor electrocardiogram signals from a patient during an ablation procedure. As shown, electrode band 444b, which is the electrode band which is most distally positioned with respect to distal end 400 of catheter, is substantially electrically coupled to outer conductor 436 through wires 462. Such a connection to outer conductor 436 is generally made as close to the distal end of outer conductor 436 as possible, as will be understood by those skilled in the art.

In one embodiment, electrode bands 444 may each have a width of approximately 0.004 inches, or approximately 1 millimeter, although the width of each electrode band 444 may vary. As previously mentioned, electrode bands 444 may be formed from substantially any suitable biocompatible, material including, but not limited to, stainless steel and iridium platinum. Typically, the location of electrode bands 444 is such that electrode bands 444 are relatively close to monopole antenna 402.

A plug 460, which is formed around body section 408 and intermediate section 410 of monopole antenna 402, is arranged to hold monopole antenna 402 with respect to flexible tubing 440. Such a plug may be molded around at least a portion of monopole antenna 402 in order to hold monopole antenna 402. As discussed above, plug 460 may be formed from any suitable, preferably biocompatible, material, which is capable of withstanding electromagnetic fields that may be produced using monopole antenna 402. By way of example, plug 460 may be formed from a material such as Teflon or polyethylene. The configuration of intermediate section 410, with respect to body section 408 and tip section 414, is arranged to hold plug 460 securely in place with respect to monopole antenna 402.

Although only a few embodiments of the present invention have been described, it should be understood that the present invention may be embodied in many other specific forms without departing from the spirit or scope of the present invention. By way of example, an ablation catheter that includes a monopole antenna which generates a substantially deep electric field with respect to the monopole antenna has been generally described as being a microwave ablation catheter. However, such a monopole antenna may be use with various other catheters including, but not limited, to catheters which operate using radio frequency waves.

While a monopole antenna has been described as being formed from a material such as stainless steel, it should be appreciated that materials used in the fabrication of a monopole antenna may vary widely. In general, monopole antenna may be formed from substantially any material having a good electrical conductivity.

The sections of a monopole antenna, namely, the tip section, the intermediate section, and the body section, may take on various shapes without departing from the spirit or the scope of the present invention. By varying the shapes of the different sections, the shape of the electric field which emanates from the monopole antenna may be varied. For example, in one embodiment, the body section of a monopole antenna may not have a tapered shape. In some cases, varying the shapes associated with a monopole antenna may still enable the generated electric field to be substantially uniform. In other cases, varying the shapes may result in the generation of relatively non-uniform electric fields. The generation of relatively non-uniform electric fields may be desirable, for instance, when a monopole antenna is to be used for an ablation procedure that requires a specifically shaped electric field. That is, the tip section, the intermediate section, and the body section of a monopole antenna may be shaped to provide electric fields of particular shapes as required for specific ablation procedures.

A transmission line, e.g., the center conductor of a co-axial cable, has generally been described as being crimped, or otherwise coupled, to the proximal end of a monopole antenna. It should be appreciated that a transmission line may be electrically coupled to the monopole antenna using various other methods, and at different locations with respect to the monopole antenna. Therefore, the present examples are to be considered as illustrative and not restrictive, and the invention is not to be limited to the details given herein, but may be modified within the scope of the appended claims.

What is claimed is:

1. An antenna structure adapted to be used in an ablation device, comprising a monopole antenna including a substantially hemispherical distal tip operably disposed at a distal end of the ablation device and having a substantially conical shape converging proximally from the distal tip for forming an outer emission surface from which electromagnetic energy is emitted in a uniform electromagnetic field pattern about the monopole antenna in response to electromagnetic energy applied thereto.

2. The antenna structure of claim 1, wherein the electromagnetic energy emitted is sufficient to ablate biological tissue.

3. The antenna structure of claim 1, wherein the antenna is encased in a biocompatible material defining an outer surface.

4. The antenna structure of claim 3, wherein the biocompatible material is selected from the group consisting of polyetrafluorethylene and polyethylene.

5. The antenna structure of claim 1, wherein the antenna is formed from stainless steel.

6. An ablation device for ablating biological tissue; comprising:

an elongated flexible tubular member adapted to be inserted in of a patient's body and having a distal end;

an electromagnetic energy conductor disposed within the tubular member for transmitting ablation energy therethrough;

a monopole antenna attached to the conductor and including a substantially hemispherical distal tip disposed at the distal end of the tubular member, the monopole antenna having a conical shape converging proximally from the distal tip to form an outer emission surface from which electromagnetic energy is emitted in a substantially uniform electromagnetic field pattern about the monopole antenna in response to electromagnetic energy supplied t the conductor.

7. The ablation device of claim 6 further comprising at least one electrode disposed near the distal end of the tubular member proximal to the antenna for sensing electrophysiological signals.

8. The ablation device of claim 6, wherein the at least one electrode is a ring electrode.

* * * * *

UNITED STATES PATENT AND TRADEMARK OFFICE
CERTIFICATE OF CORRECTION

PATENT NO. : 6,823,218 B2 Page 1 of 1
DATED : November 23, 2004
INVENTOR(S) : Dany Berube It is certified that error appears in the above-identified patent and that said Letters Patent is hereby corrected as shown below:

Column 10,
Line 30, after the word "tissue" please delete ";" and insert -- , --.
Line 33, please delete "in of a" and insert -- should be --.

Signed and Sealed this

Nineteenth Day of July, 2005

JON W. DUDAS
*Director of the United States Patent and Trademark Office*